US00PP29565P3

(12) United States Plant Patent
Smit

(10) Patent No.: US PP29,565 P3
(45) Date of Patent: Jul. 31, 2018

(54) ***PEPEROMIA* PLANT NAMED 'SAN MARINO'**

(50) Latin Name: ***Peperomia* hybrid**
Varietal Denomination: San Marino

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 15/330,454

(22) Filed: Sep. 22, 2016

(65) Prior Publication Data

US 2018/0084700 P1 Mar. 22, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

PLUTO Plant Variety Database Aug. 30, 2017. p. 1. 2017.*

* cited by examiner

*Primary Examiner* — Annette H Para

(57) ABSTRACT

A new cultivar of *Peperomia* plant named 'San Marino' that is characterized by grey-green leaves with green veins on the upper surface and red peduncles.

1 Drawing Sheet

Botanical classification: *Peperomia* hybrid.
Variety denomination: 'San Marino'.

BACKGROUND OF THE INVENTION

The present invention relates to a new and distinct cultivar of *Peperomia* plant botanically known as *Peperomia* hybrid and hereinafter referred to by the cultivar name 'San Marino'.

'San Marino' originated from the crossing of the female or seed parent, an unnamed *Peperomia marmorata* cultivar and the male or pollen parent, an unnamed *Peperomia peruviana* cultivar. The crossing was conducted in 2013 in Sappemeer, Netherlands. The resulting seeds were subsequently planted and grown. The cultivar 'San Marino' was selected by the inventor in 2014 in a controlled environment as a single plant within the progeny of the stated cross in a cultivated area of Sappemeer, Netherlands.

Asexual reproduction of the new cultivar 'San Marino' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'San Marino'. These traits in combination distinguish 'San Marino' as a new and distinct cultivar apart from other existing varieties of *Peperomia* known by the inventor.

1. *Peperomia* 'San Marino' exhibits grey-green leaves with green veins on the upper surface.
2. *Peperomia* 'San Marino' exhibits red peduncles.

The closest comparison cultivars are *Peperomia* 'Eden Rosso' (U.S. Plant Pat. No. 24,379) and *Peperomia* 'Napoli Nights' (co-pending U.S. Plant patent application). 'San Marino' is distinguishable from 'Eden Rosso' by the following characteristics:

1. *Peperomia* 'San Marino' exhibits grey-green leaves with green veins on the upper surface. In comparison, the upper leaf surface of 'Eden Rosso' is green with darker green veins.
2. *Peperomia* 'San Marino' exhibits red peduncles. In comparison, the peduncle of 'Eden Rosso' is lighter red in color.

'San Marino' is distinguishable from 'Napoli Nights' by the following characteristics:

1. *Peperomia* 'San Marino' exhibits grey-green leaves with green veins on the upper surface. In comparison, the upper leaf surface of 'Napoli Nights' is more grey in color.
2. *Peperomia* 'San Marino' exhibits leaves having a lower surface that is red. In comparison, the leaf lower surface of 'Napoli Nights' is pink-red.

'San Marino' is distinguishable from the female parent plant, by the following characteristics:

1. The leaves of 'San Marino' are grey-green on the upper surface. The leaves of the female parent plant are green on the upper surface.
2. The leaves of 'San Marino' are red on the lower surface. The leaves of the female parent plant are darker red in color on the lower surface.
3. The peduncles of *Peperomia* 'San Marino' are red. In comparison, the peduncles of the female parent plant are pink-red.

'San Marino' is distinguishable from the male parent plant by the following characteristics:

1. The leaves of 'San Marino' are smaller and more oval in shape than the leaves of the male parent plant.

2. 'San Marino' exhibits grey-green leaves on the upper surface. The leaves of the male parent plant are green on the upper surface.

BRIEF DESCRIPTION OF THE DRAWING

The accompanying photograph illustrates the distinguishing traits of *Peperomia* 'San Marino'. The photograph shows an overall view of a 35 week old plant.

The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'San Marino'. Data was collected in Sappemeer, Netherlands from 35 week old plants grown in a glass greenhouse in 15 cm. diameter containers. The time of year was Winter and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'San Marino' has not been tested under all possible conditions and phenotypic differences may be observed with variations in environmental, climatic, and cultural conditions, however, without any variance in genotype.

Botanical classification: *Peperomia* hybrid 'San Marino'.
Annual or perennial: Perennial.
Parentage: 'San Marino' is a hybrid of the female parent, an unnamed *Peperomia marmorata* cultivar and the male parent an unnamed *Peperomia peruviana* cultivar.
Plant type: Potted plant.
Growth habit: Rosette.
Plant shape: Flattened globe shaped.
Suitable container size: 7 cm. pots or larger.
Plant height: 21.5 cm.
Plant width: 31.5 cm.
Vigor: Low.
Low temperature tolerance: 5° Centigrade.
High temperature tolerance: 40° Centigrade.
Propagation: Leaf cuttings.
Time to initiate roots (summer): 10 days at 18 to 20° C.
Time to initiate roots (winter): 14 days at 18 to 20° C.
Time to produce a rooted cutting (summer): 80 days at 18 to 20° C.
Time to produce a rooted cutting (winter): 100 days at 18 to 20° C.
Growth rate: Low.
Crop time: Approximately 30 to 35 weeks in Sappemeer, Netherlands.
Root system: Fibrous.
Plant fragrance: None.
Stem:
- *Branching habit.*—Short thick stems branching into rosettes of leaves.
- *Number of main stems per plant.*—Average 10.
- *Number of lateral branches per plant.*—Average 50.
- *Lateral branch dimensions.*—1.6 cm. in length and 0.4 cm. in width.
- *Internode length.*—0.1 cm.
- *Stem shape.*—Rounded.
- *Stem texture.*—Smooth.
- *Stem pubescence.*—Absent.
- *Stem angle.*—5 degrees.
- *Stem strength.*—Moderately strong.
- *Stem color* (*young*).—183C.
- *Stem color* (*mature*).—197A.
- *Internode color* (*young*).—183C.
- *Internode color* (*mature*).—197A.

Foliage:
- *Leaf arrangement.*—Alternate.
- *Compound or single.*—Single.
- *Quantity of leaves per lateral branch.*—Average 11.
- *Leaf shape.*—Ovate.
- *Leaf aspect.*—Slightly convex to slightly carinate.
- *Leaf apex.*—Acute.
- *Leaf base.*—Truncate.
- *Leaf dimensions.*—3.8 cm. in length and 1.9 cm. in width.
- *Texture.*—Glabrous (both surfaces).
- *Leaf luster.*—Glossy (both surfaces).
- *Pubescence.*—Absent.
- *Leaf margin.*—Entire.
- *Venation pattern.*—Parallel, strongly furrowed.
- *Young leaf color* (*upper surface*).—N189C, surrounding veins N189A.
- *Young leaf color* (*lower surface*).—180A, surrounding veins 176A.
- *Mature leaf color* (*upper surface*).—189A.
- *Mature leaf color* (*lower surface*).—178A, toward base 176B.
- *Vein color* (*upper surface*).—139A.
- *Vein color* (*lower surface*).—178A.

Petiole:
- *Petiole dimensions.*—5.6 cm. in length and 0.25 cm. in diameter.
- *Petiole texture.*—Glabrous.
- *Petiole luster.*—Slightly glossy.
- *Petiole pubescence.*—Absent.
- *Petiole strength.*—Low.
- *Petiole color.*—182D with fine stripes 182A.

Flower:
- *Inflorescence type.*—Axillary spike.
- *Inflorescence dimensions.*—10.9 cm. in length and 0.3 cm. in diameter.
- *Quantity of flowers per inflorescence.*—Average 750.
- *Quantity of flowers and buds per plant.*—Average 20,000.
- *Fragrance.*—None.
- *Bud length.*—Average 0.2 mm.
- *Bud diameter.*—Average 0.2 mm.
- *Bud shape.*—Globose.
- *Bud color.*—144C.
- *Flower type and form.*—Flowers have no petals and consist of four stamens and a single pistil.
- *Flower aspect.*—Outward.
- *Flower dimensions.*—Average 0.4 mm. in diameter and 0.4 mm. in height.
- *Flower longevity.*—Approximately 1 month.
- *Persistent or self-cleaning.*—Self-cleaning.

Peduncle:
- *Peduncle dimensions.*—9.6 cm. in length and 0.2 cm. in diameter.
- *Peduncle angle.*—30 degrees from vertical.
- *Peduncle strength.*—Moderately weak.

*Peduncle texture.*—Smooth.
*Peduncle luster.*—Glossy.
*Peduncle color.*—184A and 185A.

Reproductive organs:
*Stamen number.*—4.
*Anther shape.*—Club shaped.
*Anther length.*—0.1 mm.
*Anther color.*—144C.
*Filament length.*—0.1 mm.
*Filament color.*—144C.
*Amount of pollen.*—Moderate.
*Pollen color.*—156D.
*Number of pistils.*—1.
*Pistil length.*—0.05 mm.
*Stigma shape.*—Flattened, ovate.
*Stigma dimensions.*—0.05 mm. in length and 0.2 mm. in diameter.
*Stigma color.*—144C.
*Style.*—None visible.
*Ovary color.*—144C.

Fruit and seed: 'San Marino' has not produced fruit or seed to date.

Disease and pest resistance: Disease and pest resistance has not been observed.

The invention claimed is:

1. A new and distinct variety of *Peperomia* plant named 'San Marino' as described and illustrated.

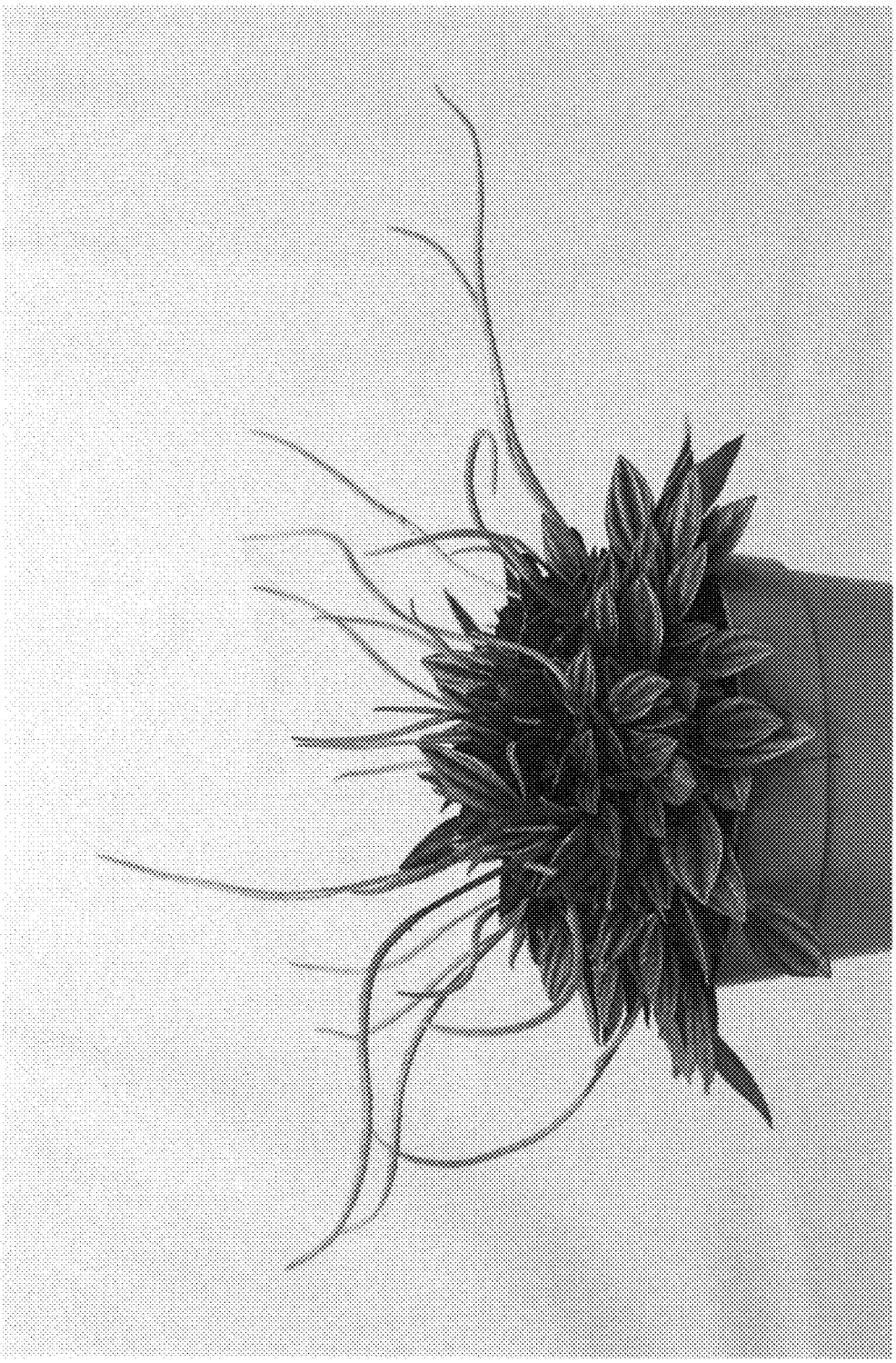

* * * * *